Oct. 23, 1962
H. T. OSBORN
Plant Pat. 2,185
CHRYSANTHEMUM PLANT
Filed Dec. 22, 1961
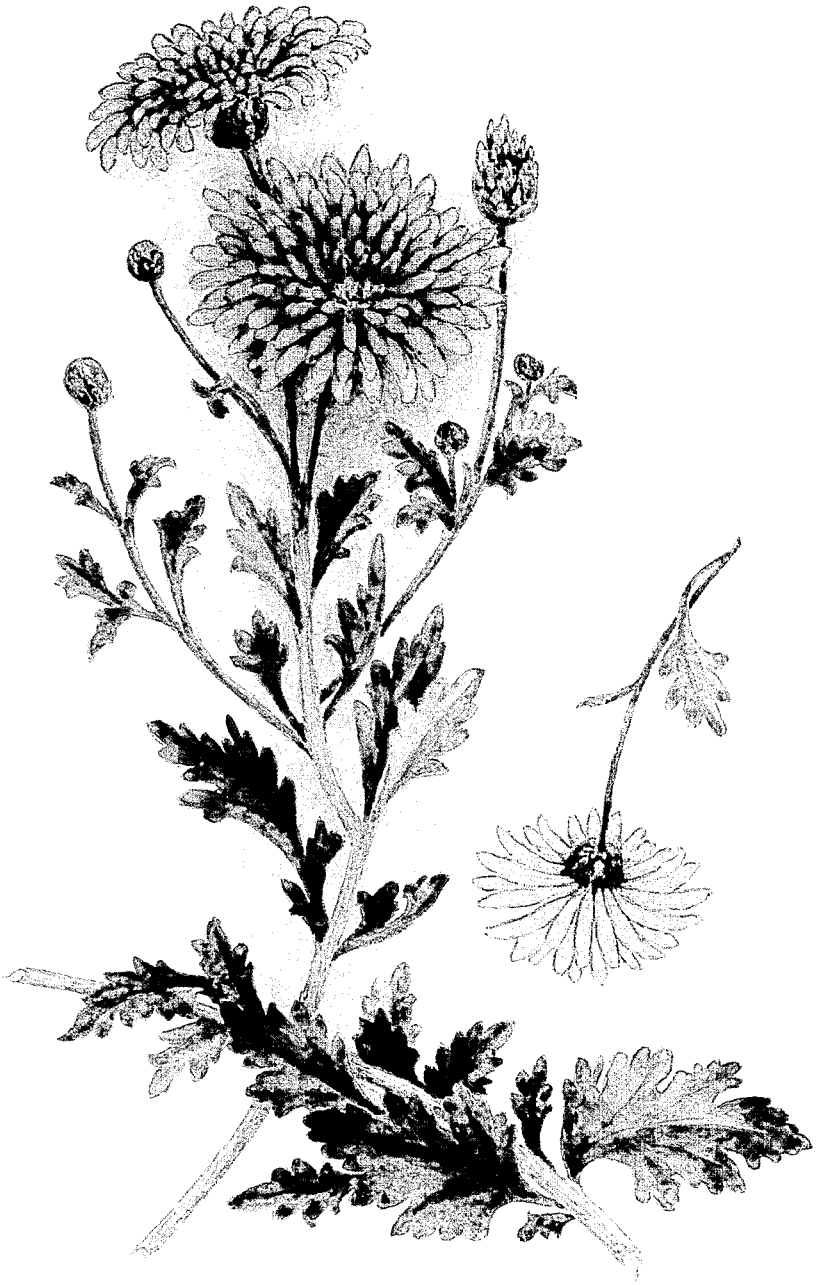
WITNESS
Addison E. Avery
INVENTOR
Hazel T. Osborn
Webster & Webster
ATTYS.

United States Patent Office

Plant Pat. 2,185
Patented Oct. 23, 1962

2,185
CHRYSANTHEMUM PLANT

Hazel T. Osborn, 5118 E. Shady Lane, Stockton, Calif.

Filed Dec. 22, 1961, Ser. No. 161,756
1 Claim. (Cl. 47—60)

The present discovery relates to a new and distinct variety of chrysanthemum plant believed to be a seedling of the variety known as Amelia (unpatented).

The discovery was made by me in the domestic garden of my residence located at Stockton, San Joaquin County, California, the variety having been found—growing as a chance seedling—in a cultivated bed where plants of the Amelia chrysanthemum had been grown.

When such plant came into bloom I recognized its distinctive character and thereafter asexually reproduced it, in my domestic garden located as aforesaid, by soft top cuttings. Such reproductions, in maturity, ran true to the parent plant in all respects.

The present variety of chrysanthemum plant generally—and rather closely—resembles the Amelia in plant structure, type of flower, time of bloom, and foliage, but has a primarily distinctive characteristic in that the flowers are an attractive uniform red of crimson shade, which color gradually lightens during opening of the flower to full bloom. In comparison, the flowers of the Amelia are magenta in color.

The plant of the instant variety of chrysanthemum is a cushion type bush, possessing decorative value in its somewhat dwarf, compact habit of growth, its sturdy appearance, and its flowers which substantially cover the bush.

Further characteristics of the variety are as follows:

The plant has sturdy flower and leaf stalks, and its many branched stalks are of adequate strength to support the profuse quantity of flowers; the latter being capable of withstanding rain and light frost.

The plant does not break down or spread ungracefully or irregularly, but maintains a substantially upright position which is of great advantage when planted individually, in a mass, or as a border.

The plant, which will tolerate some freezing of the ground and appears to have no unusual susceptibility to insects or disease, develops a compact, global shaped bush without pinching back, and when planted in sufficiently spaced-apart relation attains a maximum diameter of two feet in its first year's growth from soft top cuttings planted in early May in Stockton, California.

The foliage is healthy, attractive, and adequate in quantity for such a floriferous plant; the latter having stems, branching from the base, that can be removed to provide cut flowers for decorative use.

The flowers, which are relatively late season, begin to bloom in the fore part of November, and—while profuse—are of long lasting quality.

In the drawings:

FIG. 1 illustrates a spray, in natural color, including foliage, buds, and flowers.

FIG. 2 is a view of one of the flowers detached and inverted to show the under side color.

Referring now specifically to the physiological details of this new and distinct variety of chrysanthemum plant, the following is a detailed description thereof in outline; all major color plate identifications being by reference to Maerz and Paul Dictionary of Color, except where otherwise indicated, or where common terms of color definition are employed.

Parentage: Seedling. Seed parent—Amelia.
Class: Cushion.

*Flower*

Blooming habit: Blooms late, beginning in the fore part of November; profuse.

Bud:
- *Size.*—Small.
- *Form.*—Round.
- *Color.*—Green, opening to red.

Bloom:
- *Size.*—Small; average 1½"–2" in diameter.
- *Form.*—Flat; pompon.
- *Born.*—Singly.
- *Stems.*—Medium strength; medium length.
- *Petalage.*—Double; normally few stamens.
- *Color.*—Upper side—red of crimson shade (824/3 to 824)—The British Colour Council Horticultural Colour Chart. Color tends to lighten as flowers progress to full bloom. Under side—lighter red, with pink cast (43–J–1).
- *Discoloration.*—Not discolored by sun, rain, or light frost.
- *Texture.*—Velvety; soft but substantial.
- *Affected by hot weather.*—No.
- *Fragrance.*—Typical chrysanthemum odor.
- *Lasting quality.*—Both color and substance very durable on plant and as cut flowers.
- *Genital organs.*—Substantially all hidden in bloom; yellow.

*Plant*

Form: Cushion type bush.

Growth: Vigorous; dwarf; branching; compact. Average height—16" to 18". Maximum height—24". Average width—16" to 18". Maximum width—24".

Foliage—Leaves:
- *Quantity.*—Average for such a floriferous plant.
- *Size.*—Maximum width—1¾". Maximum length—2". Petiole—¾".
- *Texture.*—Soft.
- *Shape.*—Ovate; acute.
- *Margin.*—Serrate; incised deeply.
- *Color.*—Upper surface—medium green (23–L–7). Under surface—lighter green (21–F–4). Older leaves turn to a yellow green (12–L–1), darkening to a purple shade (47–L–6) at and adjacent the tips.

The chrysanthemum plant and its flowers as herein described may vary in slight detail due to climatic and soil conditions under which the variety may be grown; the present description being of the variety as grown at Stockton, California.

The following is claimed:

A new and distinct variety of late blooming chrysanthemum plant as illustrated and described characterized—in comparison to the Amelia and to which there is general resemblance—by small, round, soft flowers of double petalage pompon form and of a uniform red color of crimson shade, the flowers being borne profusely and being long lasting; and further characterized by its being a vigorous, dwarf, branching, compact plant of cushion type bush form.

No references cited.